United States Patent
Gustavsson et al.

(10) Patent No.: US 6,747,164 B2
(45) Date of Patent: Jun. 8, 2004

(54) USE OF AMINE COMPOUNDS WITH IMPROVED BIODEGRADABILITY AS ADJUVANTS FOR PESTICIDES AND FERTILIZERS

(75) Inventors: Bodil Gustavsson, Stora Höga (SE); Burkhard Weuste, Gummersbach (DE)

(73) Assignee: Akzo Nobel N.V., Arnhen (NL)

( * ) Notice: Subject to any disclaimer, the term of this patent is extended or adjusted under 35 U.S.C. 154(b) by 0 days.

(21) Appl. No.: 10/297,853

(22) PCT Filed: May 25, 2001

(86) PCT No.: PCT/SE01/01178

§ 371 (c)(1),
(2), (4) Date: Mar. 25, 2003

(87) PCT Pub. No.: WO01/95720

PCT Pub. Date: Dec. 20, 2001

(65) Prior Publication Data

US 2003/0176286 A1 Sep. 18, 2003

(30) Foreign Application Priority Data

Jun. 15, 2000 (SE) ............................................ 0002230

(51) Int. Cl.⁷ ............................................ C07C 233/00
(52) U.S. Cl. .................... 554/55; 424/405; 424/408; 424/409; 424/421; 514/613; 514/617; 514/625; 514/627; 514/629; 554/51; 568/606; 568/613; 568/616; 568/852
(58) Field of Search .................... 554/51, 55; 568/603, 568/613, 616, 852; 514/613, 617, 625, 627, 629; 424/405, 408, 409, 421

(56) References Cited

U.S. PATENT DOCUMENTS

| | | | |
|---|---|---|---|
| 3,836,552 A | 9/1974 | Stach et al. | 260/404.5 |
| 4,228,042 A | 10/1980 | Letton | 252/528 |
| 4,824,603 A | 4/1989 | Möller et al. | 252/545 |
| 5,958,439 A | 9/1999 | Gubelmann | 424/406 |

FOREIGN PATENT DOCUMENTS

| | | | | |
|---|---|---|---|---|
| EP | 0 257 686 A1 | 3/1988 | .......... | A01N/25/30 |
| EP | 0 265 824 A2 | 5/1988 | .......... | C07F/9/09 |
| EP | 0 638 236 A1 | 2/1995 | .......... | A01N/25/30 |
| WO | 97/05779 | 2/1997 | .......... | A01N/25/30 |
| WO | 98/47860 | 10/1998 | .......... | C07C/231/02 |
| WO | 00/08927 | 2/2000 | .......... | A01N/25/30 |
| WO | WO 01/32019 A1 | 5/2001 | .......... | A01N/25/30 |

OTHER PUBLICATIONS

International Search Report, for PCT/SE01/01178 dated Sep. 26, 2001.
Derwent Abstract No. 19770602 abstracting German Patent No.: DE 2 641 286.
Derwent Abstract No. 19971028 abstracting Japanese Patent No.: JP 9278728.
Australian Patent Abstract for: AU 749008.

Primary Examiner—Deborah D. Carr
(74) Attorney, Agent, or Firm—Ralph J. Mancini

(57) ABSTRACT

The present invention relates to the use of an amino compound, which is an esteramine or an amidoamine surfactant with improved biodegradability, as an adjuvant for agrochemically active compounds such as pesticides or fertilizers. The adjuvant has Formula (I) where R1 is an aliphatic group containing 7–22 carbon atoms; EO is an ethyleneoxy group; Y is O or NH; R2 and R3 is independently $CH_2CH_2OH$ or an alkyl group with 1–5 carbon atoms, preferably 1–3 carbon atoms; n is a number between 0–10; x is a number 0–1 provided that when Y is O, then x is 1, and when Y is NH, then x is O; and m is a number 2–6, preferably 2–3, provided that when Y is NH, then m is 3–6, preferably 3; or an adduct obtained by reacting one mole of the compound with 1–5 moles of an alkylene oxide having 2–3 carbon atoms. The esteramines are obtained from an ethoxylated alcohol that has been carboxymethylated and then esterified with a tertiary hydroxyamine (alkanolamine), and the amidoamines are obtained by reaction between a fatty acid or a fatty acid methyl ester and a diamine, such as N,N-bishydroxyethyl-1,3-propylenediamine.

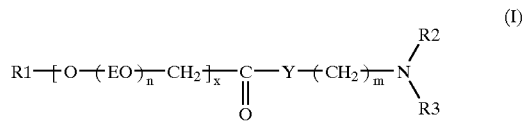

(I)

16 Claims, No Drawings

USE OF AMINE COMPOUNDS WITH IMPROVED BIODEGRADABILITY AS ADJUVANTS FOR PESTICIDES AND FERTILIZERS

The present application was filed on May 25, 2001 as international application serial number PCT/SE01/01178 and claims priority of Swedish patent application No. 0002230-1 filed on Jun. 15, 2000.

The present invention relates to the use of an amino compound, which is an esteramine or an amidoamine surfactant with improved biodegradability, as an adjuvant for agrochemically active compounds such as pesticides or fertilizers. The esteramines are obtained from an ethoxylated alcohol that has been carboxymethylated and then esterified with a tertiary hydroxyamine (alkanolamine), and the amidoamines are obtained by reaction between a fatty acid or a fatty acid methyl ester and a diamine, such as N,N-bishydroxyethyl-1,3-propylenediamine.

It is well known that the uptake as well as the efficacy of many pesticides and fertilizers can be improved by the addition of so called adjuvants. A variety of surfactants have been used for this purpose, and many of them are nitrogen containing. The surfactant group that has been most widely used in this connection is the fatty amine ethoxylates, but also other types of compounds have been described as adjuvants for pesticides or fertilizers. In EP-A1-0 638 236 is described an agricultural chemical composition containing as an adjuvant compounds of the esteramine type mentioned above. The esteramines disclosed in that publication all referred to compounds having two fatty alkyl chains. In WO 97/05779 plant protection compositions containing water-soluble active materials and one or more polyethoxylated amidoamines containing two carbon atoms between the amido and amino groups were claimed.

However, nowadays there is an increasing demand in most areas for compounds that are readily biodegradable. This is also the case within the agrochemical field, where adjuvants with a better biodegradability combined with a good ability to improve the uptake and efficacy of pesticides and fertilizers are being sought for. Thus, the purpose of the present invention is to provide adjuvants for pesticide formulations and for formulations containing fertilizers that are at least as effective as the prior used amino compounds. Another purpose is to provide adjuvants with an improved biodegradability compared to prior known amino compounds used as adjuvants.

It has now been found that compounds with the formula (I)

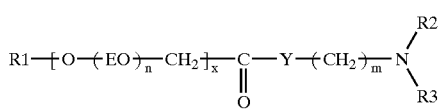

where R1 is an aliphatic group containing 7–22 carbon atoms; EO is an ethyleneoxy group; Y is O or NH; R2 and R3 is independently —CH$_2$CH$_2$OH, —CH$_2$CH(CH$_3$)OH or an alkyl group with 1–5 carbon atoms, preferably 1–3 carbon atoms; n is a number between 0–10; x is a number 0 or 1 provided that when Y is O, then x is 1, and when Y is NH, then x is 0; and m is a number 2–6, preferably 2–3, provided that when Y is NH, then m is 3–6, preferably 3; or an adduct obtained by reacting one mole of the compound with 1–5 moles of an alkylene oxide having 2–3 carbon atoms; can be used as adjuvants in agrochemical compositions. When reacting the compound of formula I and an alkylene oxide having 2–3 carbon atoms, the alkylene oxide will be added to the groups containing active hydrogen atoms, and/or will be inserted into the ester or amide groups by rearrangement reactions. The compounds of the invention are readily biodegradable and are very effective in improving the efficacy of pesticides and fertilizers. Another benefit of the compounds is that they do not show any, or very little, eye irritancy. Some of the compounds can be formulated together with a pesticide or fertilizer, giving clear solutions of low viscosity, whereas others give solutions that are of moderate viscosity or turbid. These latter solutions often separate gradually into two phases. It has been found that also in these cases stable low-viscous solutions can be obtained by the addition of an alkyl glycoside according to the formula ROG$_p$, where R is an alkyl group containing 6–10 carbon atoms, preferably 6–8, G is a monosaccharide residue and p is a number between 1–5. Surprisingly it has been found that the addition of an alkyl glycoside, besides giving rise to clear, stable solutions of low viscosity, also enhances the effect of the adjuvants of the invention. The alkyl glycosides are also readily biodegradable, so there is no disadvantage in adding them to the formulations.

Suitable examples of compounds according to the present invention are the esteramines described by the formula (II)

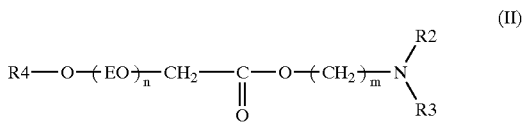

where R4 is an alkyl group containing 8–22, preferably 8–18, carbon atoms, n is 2–7, m is a number 2–3 and R2 and R3 is independently —CH$_2$CH$_2$OH, —CH$_2$CH(CH$_3$)OH or an alkyl group with 1–5, preferably 1–3 carbon atoms. N,N-Dimethylethanolamine esters of this type have been described in e.g. U.S. Pat. No. 4,228,042, where they were used as intermediates to produce quaternary surfactants for use in laundry detergent compositions.

Other suitable examples of compounds according to the present invention are the amidoamines described by the formula (III):

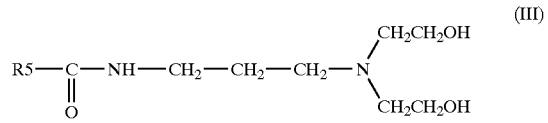

where R5 is an alkyl group containing 7–21, preferably 7–17, carbon atoms. Such amidoamines have been described in EP-A2-0 265 824, where they were used as intermediates for zwitterionic phosphate ester surfactants for use in personal care, and also in DT-A1-2641286, where they were used as intermediates for quaternary ammonium compounds for use as impregnating agents for cellulose fibre materials.

In formulations containing an active amount of the amino compounds as an adjuvant, the amount of amino compound can vary within wide limits, but is normally from 5% to 500% by weight calculated on the amount of pesticide or fertilizer present in the formulation, preferably between 10% to 200%, and most preferably between 15% to 80%.

The product (II) may easily be produced by reacting an ethercarboxylic acid according to formula (IV),

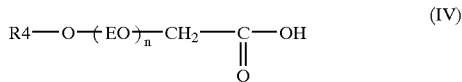

where R4 and n have the meaning mentioned above for formula II, with an alkanolamine such as N-methyldiethanolamine, triethanolamine, 3-dimethylamino-1-propanol or N,N-dimethylethanolamine. Suitable examples of hydrophobic groups R4 in formula IV are 2-ethylhexyl, octyl, decyl, coco alkyl, lauryl, oleyl, rapeseed alkyl and tallow alkyl.

The product (III) may easily be produced by reacting a fatty acid, or the methyl ester of a fatty acid, with N,N-bishydroxyethyl-1,3-propylenediamine. Suitable fatty acids are 2-ethylhexanoic acid, octanoic acid, decanoic acid, coco fatty acid, lauric acid, rapeseed fatty acid, oleic acid and tallow fatty acid. The product based on coco fatty acid is most preferred.

Suitable processes for the production of the amidoamine compounds (III) are described in e.g. WO 98/47860, DT-A1-2641286 and EP-A2-0 265 824.

The present invention also relates to certain compounds which are novel. These compounds have the formula (II), where R4 is an alkyl group containing 8–22, preferably 8–18, carbon atoms, n=2–7, m is 3 and each R2 and R3 independently of each other is an alkyl group with 1–5, preferably 1–3, carbon atoms, or the formula (II), where R4 is an alkyl group containing 8–22, preferably 8–18, carbon atoms, n=2–7, m is 2, one of the groups R2 and R3 is —CH$_2$CH$_2$OH or —CH$_2$CH(CH$_3$)OH and the other group is an alkyl group with 1–5, preferably 1–3, carbon atoms, —CH$_2$CH$_2$OH, or —CH$_2$CH(OH$_3$)OH or the formula (III), where R5 is CH$_3$(CH$_2$)$_3$CH(CH$_2$CH$_3$)—.

The amino compounds of the present invention could be added as adjuvants to both liquid, such as aqueous, and solid agricultural compositions containing pesticides, such as herbicides, acaricides, fungicides and insecticides, as well as plant growth regulators and fertilizers. The liquid composition could be in the form of a solution, a microemulsion, an emulsion or a suspension. Typical examples of herbicides are different amine salts of glyphosate, such as the isopropylamine salt, the dimethylamine salt and the ethylenediamine salts; other salts of glyphosate, such as the sesquisodium salt and the trimethylsulphonium salt; glufosinate, salts of 2,4-dichlorophenoxyacetic acid, salts of 4-chloro-2-methylphenoxyacetic acid, bialaphos, dicamba, diphenylethers, imidazolinones and sulphonyl ureas. The amino compounds of the present invention are excellent adjuvants for the water soluble herbicides, e.g. the widely used herbicide glyphosate (glyphosate=N-(phosphonomethyl)-glycine), and the salts thereof. Suitable examples of fungicides are e.g. azoxystrobin, epoxiconazole, kcresoximmethyl and propiconazole.

Other examples of formulations where the amino compounds may be used as adjuvants are micronutrient solutions containing one or several micronutrients, such as iron, manganese, copper, zinc, boron and molybdenum. The micronutrients may be complexed to e.g. aminocarboxylates, such as EDTA, DTPA, HEDTA, EDDHMA and EDDHA. In addition to micronutrients and chelating agents, the formulations may also contain macronutrients, such as nitrogen, phosphorus, potassium, magnesium and sulphur, and pesticides may also be included. These above-mentioned formulations are particularly suitable for foliar applications.

The formulations according to the invention may also contain other additives, such as other surfactants, hydrotropes and preservatives; additives to further enhance pesticidal activity, such as ammonium sulphate; solvents, corrosion inhibitors, thickeners, sequestering agents, anti-freeze agents, anti-foam agents, anti-gelling agents and dyes.

The compositions could also contain viscosity reducing agents such as glycerol, ethylene glycol, propylene glycol and low molecular weight polyethylene or polypropylene glycols.

The compositions could be concentrates as well as diluted, "ready to use", solutions. The concentrations may vary within wide limits, and a pesticide formulation could contain 0.01–99.9% by weight of a pesticide, 0–40% by weight of ammonium sulphate and an amount of 0.01–70% by weight of an amino compound according to the invention. A suitable herbicide is glyphosate, or a salt thereof, which is preferably present in an amount of 0.02–70% by weight. An adjuvant according to the present invention can also advantageously be used in combination with solid agrochemical substances such as strobilurin analogues

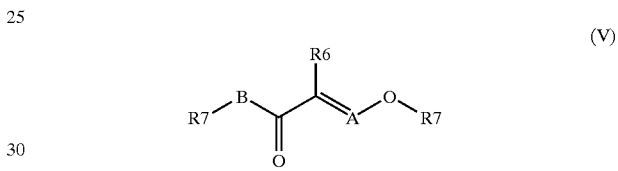

wherein R6 is an aromatic or heteroaromatic substituted or unsubstituted group, R7 is H or C$_1$–C$_{10}$ alkyl, A is CH or N and B is O or NH (e.g. azoxystrobin) and sulphonyl ureas to form granules or dispersions. The stability of the dispersions may be further enhanced by the addition of other conventional surfactants, such as nonionics, e.g. ethoxylated fatty alcohols or amines, or alkyl glycosides containing more than 10 carbon atoms in the alkyl chain. As a concentrate, the concentrations are normally in the range of 4–70% for the pesticide, 2–50% for the adjuvants and 0–40% of ammonium sulphate, whereas for the ready-to-use solutions the corresponding ranges are 0.01–4%, 0.01–8% and 0–40%. The components could all be mixed in the concentrate or be tank-mixed just before spraying the solution.

A fertilizer formulation could contain 0.0001–99.9%, preferably 0.001–99.9%, by weight of a fertilizer and an amount of 0.0001–70%, preferably 0.001–70%, by weight of an amino compound according to the invention. In a ready-to-use formulation the concentration of micronutrients are usually in the lower area of the range.

The following examples are illustrative of the invention and are not to be construed as a limitation of the scope.

EXAMPLE 1

Biodegradability tests were performed with the "closed bottle test" as described in OECD Test 301D. A number of amino adjuvant compounds according to the invention were compared with a diester amino compound and a monoamide compound between coco fatty acid and ethylenediamine that had been ethoxylated with 2 moles of EO. The biodegradability values obtained after 28 days for the above-mentioned compounds are displayed in Table 1.

TABLE 1

Biodegradability values obtained by the OECD Test 301D.

| Compound | Biodegradability (%) |
| --- | --- |
| Cocoamide of N,N-bishydroxyethyl-1,3-propylenediamine | 67 |
| Monoester between polyethyleneglycol (4.5 EO)-monococo ether monocarboxymethyl ether and N-methyldiethanolamine | 75 |
| Monoester between polyethyleneglycol (4.5 EO)-monococo ether monocarboxymethyl ether and triethanolamine | 75 |
| Monoester between polyethyleneglycol (2.5 EO)-monococo ether monocarboxymethyl ether and triethanolamine | 82 |
| Ester between polyethyleneglycol (4.5 EO)-monococo ether monocarboxymethyl ether and 3-dimethylamino-1-propanol | 67 |
| Diester between polyethyleneglycol (4.5 EO)-monococo ether monocarboxymethyl ether and N-methyldiethanolamine (Comparative example) | 21 |
| Monococoamide of ethylenediamine ethoxylated with 2 moles of EO (Comparative example) | 44 |

From these results it is evident that the amino compound adjuvants of the present invention exhibit a better biodegradability than the two-chained esteramine and the aminoamide derived from ethylenediamine that were used as references.

EXAMPLE 2

The herbicidal effects of formulations containing the herbicide glyphosate and amino compounds according to the present invention were investigated in greenhouse tests. For comparison, formulations containing a diester amino compound were included in the investigation.

Roundup® (a commercially available herbicidal standard formulation from Monsanto), which contains the isopropylamine salt of glyphosate and an ethoxylated fatty amine, was also included as a reference. In Roundup® the weight ratio adjuvant/glyphosate is 1:2.

The weeds used were glasshouse grown *Elymus repens*, *Brassica napus* and *Lolium rigidum*. The treatments for *Elymus repens* and *Brassica napus* were sprayed at three dose rates; 0.15, 0.25 and 0.75 kg a.e./ha referring to glyphosate, and for *Lolium rigidum* the doses were 0.08, 0.15 and 0.25 kg a.e./ha referring to glyphosate. The recommended dose rate for glyphosate is 1.08 kg a.e./ha. There were three replicates of each treatment.

The aqueous herbicide formulations were sprayed on the plants by using a laboratory track sprayer fitted with an 80015E flat fan nozzle, at a spray pressure of 210 kPA delivering 202 litres/ha.

The following formulation recipes were used for the greenhouse tests displayed in Tables 3–8. In some formulations also hexyl or 2-ethylhexyl glucoside was added, and in those cases the amount of adjuvant stated in the recipes below also includes the amount of glucoside. All formulations were diluted with water before spraying. The concentrations of the diluted solutions are displayed in Table 1 and 2 further below.

Formulation (Concentrated, Glyphosate:Adjuvant 2:1)

| Glyphosate isopropyl-amine salt | 13.8% w/w a.e. |
| --- | --- |
| Amino compound adjuvant | 6.9% w/w |
| Water | balance |

The formulation was clear and stable.

Formulation (High-Concentrated, Glyphosate:Adjuvant 5:1)

| Glyphosate isopropyl-amine salt | 40.7% w/w a.e. |
| --- | --- |
| Amino compound adjuvant | 8.3% w/w |
| Water | balance |

The formulation was clear and stable.

Formulation (High-Concentrated, Glyphosate:Adjuvant 2:1)

| Glyphosate isopropyl-amine salt | 30.5% w/w a.e. |
| --- | --- |
| Amino compound adjuvant | 15.2% w/w |
| Water | balance |

The formulation was clear and stable.

The diluted solutions that were sprayed had the concentrations displayed in the tables below.

TABLE 1

Ratio glyphosate/adjuvant[1] 2:1

| Dose rate (kg/ha) | Concentration of glyphosate acid equivalents (%) | Concentration of adjuvant[1] (%) |
| --- | --- | --- |
| 0.75 | 0.37 | 0.18 |
| 0.25 | 0.12 | 0.06 |
| 0.15 | 0.07 | 0.04 |
| 0.08 | 0.04 | 0.02 |

[1]or adjuvant + alkyl glucoside whenever applicable.

TABLE 2

Ratio glyphosate/adjuvant[2] ca 5:1

| Dose rate (kg/ha) | Concentration of glyphosate acid equivalents (%) | Concentration of adjuvant[2] (%) |
| --- | --- | --- |
| 0.75 | 0.37 | 0.075 |
| 0.25 | 0.12 | 0.025 |
| 0.15 | 0.07 | 0.014 |
| 0.08 | 0.04 | 0.008 |

[2]or adjuvant + alkyl glucoside whenever applicable.

The experiments were assessed according to the amount of green life growth and regrowth 5 weeks after spraying for *Elymus repens* and 4 weeks after spraying for *Brassica napus* and *Lolium rigidum*. A score of 0–100% was used, where 100% is a totally dead plant, and for example a 50% reduction in the amount of green growth present was scored by a comparison to the best untreated plant, the latter scoring 0%.

TABLE 3

Greenhouse test with *Elymus repens*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/adjuvant ratio |
|---|---|---|---|
| Cocoamide of N,N-bishydroxyethyl-1,3-propylenediamine | 0.15 | 13 | 2:1 |
| Cocoamide of N,N-bishydroxyethyl-1,3-propylenediamine | 0.25 | 75 | 2:1 |
| Cocoamide of N,N-bishydroxyethyl-1,3-propylenediamine | 0.75 | 97 | 2:1 |
| Cocoamide of N,N-bishydroxyethyl-1,3-propylenediamine | 0.15 | 8 | 5:1 |
| Cocoamide of N,N-bishydroxyethyl-1,3-propylenediamine | 0.25 | 65 | 5:1 |
| Cocoamide of N,N-bishydroxyethyl-1,3-propylenediamine | 0.75 | 95 | 5:1 |
| 80% Cocoamide of N,N-bishydroxyethyl-1,3-propylenediamine + 20% hexyl glucoside | 0.15 | 17 | 2:1 |
| 80% Cocoamide of N,N-bishydroxyethyl-1,3-propylenediamine + 20% hexyl glucoside | 0.25 | 80 | 2:1 |
| 80% Cocoamide of N,N-bishydroxyethyl-1,3-propylenediamine + 20% hexyl glucoside | 0.75 | 97 | 2:1 |
| 50% Cocoamide of N,N-bishydroxyethyl-1,3-propylenediamine + 50% 2-ethylhexyl glucoside | 0.15 | 13 | 2:1 |
| 50% Cocoamide of N,N-bishydroxyethyl-1,3-propylenediamine + 50% 2-ethylhexyl glucoside | 0.25 | 72 | 2:1 |
| 50% Cocoamide of N,N-bishydroxyethyl-1,3-propylenediamine + 50% 2-ethylhexyl glucoside | 0.75 | 98 | 2:1 |
| 80% Cocoamide of N,N-bishydroxyethyl-1,3-propylenediamine + 20% 2-ethylhexyl glucoside | 0.15 | 13 | 5:1 |
| 80% Cocoamide of N,N-bishydroxyethyl-1,3-propylenediamine + 20% 2-ethylhexyl glucoside | 0.25 | 57 | 5:1 |
| 80% Cocoamide of N,N-bishydroxyethyl-1,3-propylenediamine + 20% 2-ethylhexyl glucoside | 0.75 | 93 | 5:1 |
| 80% Cocoamide of N,N-bishydroxyethyl-1,3-propylenediamine + 20% hexyl glucoside | 0.15 | 8 | 5:1 |
| 80% Cocoamide of N,N-bishydroxyethyl-1,3-propylenediamine + 20% hexyl glucoside | 0.25 | 50 | 5:1 |
| 80% Cocoamide of N,N-bishydroxyethyl-1,3-propylenediamine + 20% hexyl glucoside | 0.75 | 95 | 5:1 |
| Cocoamide of N,N-bishydroxyethyl-1,3-propylenediamine + ammonium sulphate (3% w/w of the concentrate) | 0.15 | 27 | 5:1 |
| Cocoamide of N,N-bishydroxyethyl-1,3-propylenediamine + ammonium sulphate (3% w/w of the concentrate) | 0.25 | 67 | 5:1 |
| Cocoamide of N,N-bishydroxyethyl-1,3-propylenediamine + ammonium sulphate (3% w/w of the concentrate) | 0.75 | 95 | 5:1 |
| 50% 2-Ethylhexylamide of N,N-bishydroxyethyl-1,3-propylenediamine + 50% hexyl glucoside | 0.15 | 10 | 2:1 |
| 50% 2-Ethylhexylamide of N,N-bishydroxyethyl-1,3-propylenediamine + 50% hexyl glucoside | 0.25 | 38 | 2:1 |
| 50% 2-Ethylhexylamide of N,N-bishydroxyethyl-1,3-propylenediamine + 50% hexyl glucoside | 0.75 | 92 | 2:1 |
| 50% Oleylamide of N,N-bishydroxyethyl-1,3-propylenediamine + 50% hexyl glucoside | 0.15 | 13 | 2:1 |
| 50% Oleylamide of N,N-bishydroxyethyl-1,3-propylenediamine + 50% hexyl glucoside | 0.25 | 73 | 2:1 |
| 50% Oleylamide of N,N-bishydroxyethyl-1,3-propylenediamine + 50% hexyl glucoside | 0.75 | 92 | 2:1 |
| Ester between polyethyleneglycol (4.5 EO)-monococo ether monocarboxymethyl ether and 3-dimethylamino-1-propanol | 0.15 | 17 | 2:1 |
| Ester between polyethyleneglycol (4.5 EO)-monococo ether monocarboxymethyl ether and 3-dimethylamino-1-propanol | 0.25 | 73 | 2:1 |
| Ester between polyethyleneglycol (4.5 EO)-monococo ether monocarboxymethyl ether and 3-dimethylamino-1-propanol | 0.75 | 93 | 2:1 |
| 50% Diester between polyethyleneglycol (4.5 EO)-monococo ether monocarboxymethyl ether and N-methyldiethanolamine + 50% hexyl glucoside (Reference) | 0.15 | 5 | 2:1 |
| 50% Diester between polyethyleneglycol (4.5 EO)-monococo ether monocarboxymethyl ether and N-methyldiethanolamine + 50% hexyl glucoside (Reference) | 0.25 | 67 | 2:1 |
| 50% Diester between polyethyleneglycol (4.5 EO)-monococo ether monocarboxymethyl ether and N-methyldiethanolamine + 50% hexyl glucoside (Reference) | 0.75 | 92 | 2:1 |
| Ester between polyethyleneglycol (4.5 EO)-monococo ether monocarboxymethyl ether and 3-dimethylamino-1-propanol | 0.15 | 10 | 5:1 |
| Ester between polyethyleneglycol (4.5 EO)-monococo ether | 0.25 | 58 | 5:1 |

TABLE 3-continued

Greenhouse test with *Elymus repens*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| monocarboxymethyl ether and 3-dimethylamino-1-propanol Ester between polyethyleneglycol (4.5 EO)-monococo ether monocarboxymethyl ether and 3-dimethylamino-1-propanol | 0.75 | 92 | 5:1 |
| 50% Diester between polyethyleneglycol (4.5 EO)-monococo ether monocarboxymethyl ether and N-methyldiethanolamine + 50% hexyl glucoside (Reference) | 0.15 | 3 | 5:1 |
| 50% Diester between polyethyleneglycol (4.5 EO)-monococo ether monocarboxymethyl ether and N-methyldiethanolamine + 50% hexyl glucoside (Reference) | 0.25 | 40 | 5:1 |
| 50% Diester between polyethyleneglycol (4.5 EO)-monococo ether monocarboxymethyl ether and N-methyldiethanolamine + 50% hexyl glucoside (Reference) | 0.75 | 92 | 5:1 |
| Roundup | 0.15 | 15 | 2:1 |
| Roundup | 0.25 | 72 | 2:1 |
| Roundup | 0.75 | 98 | 2:1 |

TABLE 4

Greenhouse test with *Brassica napus*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| Cocoamide of N,N-bishydroxy-ethyl-1,3-propylenediamine | 0.15 | 40 | 2:1 |
| Cocoamide of N,N-bishydroxy-ethyl-1,3-propylenediamine | 0.25 | 70 | 2:1 |
| Cocoamide of N,N-bishydroxy-ethyl-1,3-propylenediamine | 0.75 | 98 | 2:1 |
| Cocoamide of N,N-bishydroxy-ethyl-1,3-propylenediamine | 0.15 | 8 | 5:1 |
| Cocoamide of N,N-bishydroxy-ethyl-1,3-propylenediamine | 0.25 | 73 | 5:1 |
| Cocoamide of N,N-bishydroxy-ethyl-1,3-propylenediamine | 0.75 | 87 | 5:1 |
| 80% Cocoamide of N,N-bishydroxyethyl-1,3-propylenediamine + 20% hexyl glucoside | 0.15 | 25 | 2:1 |
| 80% Cocoamide of N,N-bishydroxyethyl-1,3-propylenediamine + 20% hexyl glucoside | 0.25 | 68 | 2:1 |
| 80% Cocoamide of N,N-bishydroxyethyl-1,3-propylenediamine + 20% hexyl glucoside | 0.75 | 93 | 2:1 |
| 50% Cocoamide of N,N-bishydroxyethyl-1,3-propylenediamine + 50% 2-ethylhexyl glucoside | 0.15 | 37 | 2:1 |
| 50% Cocoamide of N,N-bishydroxyethyl-1,3-propylenediamine + 50% 2-ethylhexyl glucoside | 0.25 | 68 | 2:1 |
| 50% Cocoamide of N,N-bishydroxyethyl-1,3-propylenediamine + 50% 2-ethylhexyl glucoside | 0.75 | 93 | 2:1 |
| 80% Cocoamide of N,N-bishydroxyethyl-1,3-propylenediamine + 20% 2-ethylhexyl glucoside | 0.15 | 35 | 5:1 |
| 80% Cocoamide of N,N-bishydroxyethyl-1,3-propylenediamine + 20% 2-ethylhexyl glucoside | 0.25 | 57 | 5:1 |
| 80% Cocoamide of N,N-bishydroxyethyl-1,3-propylenediamine + 20% 2-ethylhexyl glucoside | 0.75 | 95 | 5:1 |
| 80% Cocoamide of N,N-bishydroxyethyl-1,3-propylenediamine + 20% hexyl glucoside | 0.15 | 17 | 5:1 |
| 80% Cocoamide of N,N-bishydroxyethyl-1,3-propylenediamine + 20% hexyl glucoside | 0.25 | 67 | 5:1 |
| 80% Cocoamide of N,N-bishydroxyethyl-1,3-propylenediamine + 20% hexyl glucoside | 0.75 | 93 | 5:1 |
| Cocoamide of N,N-bishydroxy-ethyl-1,3-propylenediamine + ammonium sulphate (3% w/w of the concentrate) | 0.15 | 60 | 5:1 |
| Cocoamide of N,N-bishydroxy-ethyl-1,3-propylenediamine + ammonium sulphate (3% w/w of the concentrate) | 0.25 | 72 | 5:1 |
| Cocoamide of N,N-bishydroxy-ethyl-1,3-propylenediamine + ammonium sulphate (3% w/w of the concentrate) | 0.75 | 93 | 5:1 |
| 50% 2-Ethylhexylamide of N,N-bishydroxyethyl-1,3-propylenediamine + 50% hexyl glucoside | 0.15 | 20 | 2:1 |
| 50% 2-Ethylhexylamide of N,N-bishydroxyethyl-1,3-propylenediamine + 50% hexyl glucoside | 0.25 | 52 | 2:1 |
| 50% 2-Ethylhexylamide of N,N-bishydroxyethyl-1,3-propylenediamine + 50% hexyl glucoside | 0.75 | 92 | 2:1 |
| 50% Oleylamide of N,N-bishydroxyethyl-1,3-propylenediamine + 50% hexyl glucoside | 0.15 | 15 | 2:1 |
| 50% Oleylamide of N,N-bishydroxyethyl-1,3-propylenediamine + 50% hexyl glucoside | 0.25 | 62 | 2:1 |
| 50% Oleylamide of N,N-bishydroxyethyl-1,3-propylenediamine + | 0.75 | 83 | 2:1 |

TABLE 4-continued

Greenhouse test with *Brassica napus*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| propylenediamine + 50% hexyl glucoside | | | |
| Ester between polyethyleneglycol (4.5 EO)-monococo ether monocarboxymethyl ether and 3-dimethylamino-1-propanol | 0.15 | 17 | 2:1 |
| Ester between polyethyleneglycol (4.5 EO)-monococo ether monocarboxymethyl ether and 3-dimethylamino-1-propanol | 0.25 | 73 | 2:1 |
| Ester between polyethyleneglycol (4.5 EO)-monococo ether monocarboxymethyl ether and 3-dimethylamino-1-propanol | 0.75 | 92 | 2:1 |
| 50% Diester between polyethyleneglycol (4.5 EO)-monococo ether monocarboxymethyl ether and N-methyldiethanolamine + 50% hexyl glucoside (Reference) | 0.15 | 17 | 2:1 |
| 50% Diester between polyethyleneglycol (4.5 EO)-monococo ether monocarboxymethyl ether and N-methyldiethanolamine + 50% hexyl glucoside (Reference) | 0.25 | 63 | 2:1 |
| 50% Diester between polyethyleneglycol (4.5 EO)-monococo ether monocarboxymethyl ether and N-methyldiethanolamine + 50% hexyl glucoside (Reference) | 0.75 | 93 | 2:1 |
| Ester between polyethyleneglycol (4.5 EO)-monococo ether monocarboxymethyl ether and 3-dimethylamino-1-propanol | 0.15 | 15 | 5:1 |
| Ester between polyethyleneglycol (4.5 EO)-monococo ether monocarboxymethyl ether and 3-dimethylamino-1-propanol | 0.25 | 62 | 5:1 |
| Ester between polyethyleneglycol (4.5 EO)-monococo ether monocarboxymethyl ether and 3-dimethylamino-1-propanol | 0.75 | 97 | 5:1 |
| 50% Diester between polyethyleneglycol (4.5 EO)-monococo ether monocarboxymethyl ether and N-methyldiethanolamine + 50% hexyl glucoside (Reference) | 0.15 | 28 | 5:1 |
| 50% Diester between polyethyleneglycol (4.5 EO)-monococo ether monocarboxymethyl ether and N-methyldiethanolamine + 50% hexyl glucoside (Reference) | 0.25 | 57 | 5:1 |
| 50% Diester between polyethyleneglycol (4.5 EO)-monococo ether monocarboxymethyl ether and N-methyldiethanolamine + 50% hexyl glucoside (Reference) | 0.75 | 92 | 5:1 |
| Hexyl glucoside (Reference) | 0.75 | 57 | 2:1 |
| 2-ethylhexyl glucoside (Reference) | 0.75 | 63 | 2:1 |
| Roundup | 0.15 | 27 | 2:1 |
| Roundup | 0.25 | 67 | 2:1 |
| Roundup | 0.75 | 95 | 2:1 |

TABLE 5

Greenhouse test with *Lolium rigidum*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| Cocoamide of N,N-bishydroxy-ethyl-1,3-propylenediamine | 0.08 | 57 | 2:1 |
| Cocoamide of N,N-bishydroxy-ethyl-1,3-propylenediamine | 0.15 | 78 | 2:1 |
| Cocoamide of N,N-bishydroxy-ethyl-1,3-propylenediamine | 0.25 | 97 | 2:1 |
| Cocoamide of N,N-bishydroxy-ethyl-1,3-propylenediamine | 0.08 | 23 | 5:1 |
| Cocoamide of N,N-bishydroxy-ethyl-1,3-propylenediamine | 0.15 | 72 | 5:1 |
| Cocoamide of N,N-bishydroxy-ethyl-1,3-propylenediamine | 0.25 | 88 | 5:1 |
| 80% Cocoamide of N,N-bishydroxyethyl-1,3-propylenediamine + 20% hexyl glucoside | 0.08 | 18 | 2:1 |
| 80% Cocoamide of N,N-bishydroxyethyl-1,3-propylenediamine + 20% hexyl glucoside | 0.15 | 60 | 2:1 |
| 80% Cocoamide of N,N-bishydroxyethyl-1,3-propylenediamine + 20% hexyl glucoside | 0.25 | 88 | 2:1 |
| 50% Cocoamide of N,N-bishydroxyethyl-1,3-propylenediamine + 50% 2-ethylhexyl glucoside | 0.08 | 17 | 2:1 |
| 50% Cocoamide of N,N-bishydroxyethyl-1,3-propylenediamine + 50% 2-ethylhexyl glucoside | 0.15 | 62 | 2:1 |
| 50% Cocoamide of N,N-bishydroxyethyl-1,3-propylenediamine + 50% 2-ethylhexyl glucoside | 0.25 | 97 | 2:1 |
| 80% Cocoamide of N,N-bishydroxyethyl-1,3-propylenediamine + 20% 2-ethylhexyl glucoside | 0.08 | 60 | 5:1 |
| 80% Cocoamide of N,N-bishydroxyethyl-1,3-propylenediamine + 20% 2-ethylhexyl glucoside | 0.15 | 62 | 5:1 |

TABLE 5-continued

Greenhouse test with *Lolium rigidum*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| 80% Cocoamide of N,N-bishydroxyethyl-1,3-propylenediamine + 20% 2-ethylhexyl glucoside | 0.25 | 87 | 5:1 |
| 80% Cocoamide of N,N-bishydroxyethyl-1,3-propylenediamine + 20% hexyl glucoside | 0.08 | 52 | 5:1 |
| 80% Cocoamide of N,N-bishydroxyethyl-1,3-propylenediamine + 20% hexyl glucoside | 0.15 | 47 | 5:1 |
| 80% Cocoamide of N,N-bishydroxyethyl-1,3-propylenediamine + 20% hexyl glucoside | 0.25 | 80 | 5:1 |
| Cocoamide of N,N-bishydroxyethyl-1,3-propylenediamine + ammonium sulphate (3% w/w of the concentrate) | 0.08 | 15 | 5:1 |
| Cocoamide of N,N-bishydroxyethyl-1,3-propylenediamine + ammonium sulphate (3% w/w of the concentrate) | 0.15 | 53 | 5:1 |
| Cocoamide of N,N-bishydroxyethyl-1,3-propylenediamine + ammonium sulphate (3% w/w of the concentrate) | 0.25 | 65 | 5:1 |
| 50% 2-Ethylhexylamide of N,N-bishydroxyethyl-1,3-propylenediamine + 50% hexyl glucoside | 0.08 | 43 | 2:1 |
| 50% 2-Ethylhexylamide of N,N-bishydroxyethyl-1,3-propylenediamine + 50% hexyl glucoside | 0.15 | 50 | 2:1 |
| 50% 2-Ethylhexylamide of N,N-bishydroxyethyl-1,3-propylenediamine + 50% hexyl glucoside | 0.25 | 88 | 2:1 |
| 50% Oleylamide of N,N-bishydroxyethyl-1,3-propylenediamine + 50% hexyl glucoside | 0.08 | 13 | 2:1 |
| 50% Oleylamide of N,N-bishydroxyethyl-1,3-propylenediamine + 50% hexyl glucoside | 0.15 | 35 | 2:1 |
| 50% Oleylamide of N,N-bishydroxyethyl-1,3-propylenediamine + 50% hexyl glucoside | 0.25 | 70 | 2:1 |
| Ester between polyethyleneglycol (4.5 EO)-monococo ether monocarboxymethyl ether and 3-dimethylamino-1-propanol | 0.08 | 12 | 2:1 |
| Ester between polyethyleneglycol (4.5 EO)-monococo ether monocarboxymethyl ether and 3-dimethylamino-1-propanol | 0.15 | 48 | 2:1 |
| Ester between polyethyleneglycol (4.5 EO)-monococo ether monocarboxymethyl ether and 3-dimethylamino-1-propanol | 0.25 | 87 | 2:1 |
| 50% Diester between polyethyleneglycol (4.5 EO)-monococo ether monocarboxymethyl ether and N-methyldiethanolamine + 50% hexyl glucoside (Reference) | 0.08 | 27 | 2:1 |
| 50% Diester between polyethyleneglycol (4.5 EO)-monococo ether monocarboxymethyl ether and N-methyldiethanolamine + 50% hexyl glucoside (Reference) | 0.15 | 57 | 2:1 |
| 50% Diester between polyethyleneglycol (4.5 EO)-monococo ether monocarboxymethyl ether and N-methyldiethanolamine + 50% hexyl glucoside (Reference) | 0.25 | 75 | 2:1 |
| Ester between polyethyleneglycol (4.5 EO)-monococo ether monocarboxymethyl ether and 3-dimethylamino-1-propanol | 0.08 | 48 | 5:1 |
| Ester between polyethyleneglycol (4.5 EO)-monococo ether monocarboxymethyl ether and 3-dimethylamino-1-propanol | 0.15 | 80 | 5:1 |
| Ester between polyethyleneglycol (4.5 EO)-monococo ether monocarboxymethyl ether and 3-dimethylamino-1-propanol | 0.25 | 93 | 5:1 |
| 50% Diester between polyethyleneglycol (4.5 EO)-monococo ether monocarboxymethyl ether and N-methyldiethanolamine + 50% hexyl glucoside (Reference) | 0.08 | 8 | 5:1 |
| 50% Diester between polyethyleneglycol (4.5 EO)-monococo ether monocarboxymethyl ether and N-methyldiethanolamine + 50% hexyl glucoside (Reference) | 0.15 | 33 | 5:1 |
| 50% Diester between polyethyleneglycol (4.5 EO)-monococo ether monocarboxymethyl ether and N-methyldiethanolamine + 50% hexyl glucoside (Reference) | 0.25 | 70 | 5:1 |
| Roundup | 0.08 | 37 | 2:1 |
| Roundup | 0.15 | 45 | 2:1 |
| Roundup | 0.25 | 88 | 2:1 |

As is shown from the tables, the amino compound adjuvants according to the present invention are comparable or more efficient adjuvants for the herbicide than the amino compound containing two alkyl chains. The formulations based on the amino compound adjuvants also exhibit comparable or better herbicidal efficacy than the Roundup formulation.

EXAMPLE 3

Greenhouse tests were performed as described in example 2, with the exception that the amount of green life and regrowth was assessed 7 weeks after spraying for *Elymus repens*. Roundup was included as a reference.

TABLE 6

Greenhouse test with *Elymus repens*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| Cocoamide of N,N-bishydroxy-ethyl-1,3-propylenediamine | 0.15 | 33 | 2:1 |
| Cocoamide of N,N-bishydroxy-ethyl-1,3-propylenediamine | 0.25 | 47 | 2:1 |
| Cocoamide of N,N-bishydroxy-ethyl-1,3-propylenediamine | 0.75 | 100 | 2:1 |
| Monoester between polyethyleneglycol (4.5 EO) monococo ether monocarboxymethyl ether and N-methyldiethanolamine | 0.15 | 37 | 2:1 |
| Monoester between polyethyleneglycol (4.5 EO) monococo ether monocarboxymethyl ether and N-methyldiethanolamine | 0.25 | 83 | 2:1 |
| Monoester between polyethyleneglycol (4.5 EO) monococo ether monocarboxymethyl ether and N-methyldiethanolamine | 0.75 | 98 | 2:1 |
| Monoester between polyethyleneglycol (4.5 EO) monococo ether monocarboxymethyl ether and triethanolamine | 0.15 | 28 | 2:1 |
| Monoester between polyethyleneglycol (4.5 EO) monococo ether monocarboxymethyl ether and triethanolamine | 0.25 | 75 | 2:1 |
| Monoester between polyethyleneglycol (4.5 EO) monococo ether monocarboxymethyl ether and triethanolamine | 0.75 | 100 | 2:1 |
| Monoester between polyethyleneglycol (2.5 EO) monococo ether monocarboxymethyl ether and triethanolamine | 0.15 | 35 | 2:1 |
| Monoester between polyethyleneglycol (2.5 EO) monococo ether monocarboxymethyl ether and triethanolamine | 0.25 | 43 | 2:1 |
| Monoester between polyethyleneglycol (2.5 EO) monococo ether monocarboxymethyl ether and triethanolamine | 0.75 | 100 | 2:1 |
| 50% Monoester between polyethyleneglycol (4.5 EO) monococo ether monocarboxymethyl ether and N-methyldiethanolamine + 50% hexyl glucoside | 0.15 | 65 | 2:1 |
| 50% Monoester between polyethyleneglycol (4.5 EO) monococo ether monocarboxymethyl ether and N-methyldiethanolamine + 50% hexyl glucoside | 0.25 | 77 | 2:1 |
| 50% Monoester between polyethyleneglycol (4.5 EO) monococo ether monocarboxymethyl ether and N-methyldiethanolamine + 50% hexyl glucoside | 0.75 | 100 | 2:1 |
| Roundup | 0.15 | 15 | 2:1 |
| Roundup | 0.25 | 27 | 2:1 |
| Roundup | 0.75 | 97 | 2:1 |

TABLE 7

Greenhouse test with *Brassica napus*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| Cocoamide of N,N-bishydroxy-ethyl-1,3-propylenediamine | 0.15 | 45 | 2:1 |
| Cocoamide of N,N-bishydroxy-ethyl-1,3-propylenediamine | 0.25 | 52 | 2:1 |
| Cocoamide of N,N-bishydroxy-ethyl-1,3-propylenediamine | 0.75 | 90 | 2:1 |
| Monoester between polyethyleneglycol (4.5 EO) monococo ether monocarboxymethyl ether and N-methyldiethanolamine | 0.15 | 55 | 2:1 |
| Monoester between polyethyleneglycol (4.5 EO) monococo ether monocarboxymethyl ether and N-methyldiethanolamine | 0.25 | 70 | 2:1 |
| Monoester between polyethyleneglycol (4.5 EO) monococo ether monocarboxymethyl ether and N-methyldiethanolamine | 0.75 | 92 | 2:1 |
| Monoester between polyethyleneglycol (4.5 EO) monococo ether monocarboxymethyl ether and triethanolamine | 0.15 | 58 | 2:1 |
| Monoester between polyethyleneglycol (4.5 EO) monococo ether monocarboxymethyl ether and triethanolamine | 0.25 | 75 | 2:1 |
| Monoester between polyethyleneglycol (4.5 EO) monococo ether monocarboxymethyl ether and triethanolamine | 0.75 | 92 | 2:1 |
| Monoester between polyethyleneglycol (2.5 EO) monococo ether monocarboxymethyl ether and triethanolamine | 0.15 | 42 | 2:1 |
| Monoester between polyethyleneglycol (2.5 EO) monococo ether monocarboxymethyl ether and triethanolamine | 0.25 | 52 | 2:1 |
| Monoester between polyethyleneglycol (2.5 EO) monococo ether monocarboxymethyl ether and triethanolamine | 0.75 | 90 | 2:1 |

TABLE 7-continued

Greenhouse test with *Brassica napus*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| triethanolamine | | | |
| 50% Monoester between polyethyleneglycol (4.5 EO) monococo ether monocarboxymethyl ether and N-methyldiethanolamine + 50% hexyl glucoside | 0.15 | 67 | 2:1 |
| 50% Monoester between polyethyleneglycol (4.5 EO) monococo ether monocarboxymethyl ether and N-methyldiethanolamine + 50% hexyl glucoside | 0.25 | 57 | 2:1 |
| 50% Monoester between polyethyleneglycol (4.5 EO) monococo ether monocarboxymethyl ether and N-methyldiethanolamine + 50% hexyl glucoside | 0.75 | 95 | 2:1 |
| Roundup | 0.15 | 45 | 2:1 |
| Roundup | 0.25 | 65 | 2:1 |
| Roundup | 0.75 | 87 | 2:1 |

TABLE 8

Greenhouse test with *Lolium rigidum*. The dose rates are referring to the amount of glyphosate, the amount of adjuvant or adjuvant/glucoside mixture being half or one fifth of that amount.

| Adjuvant | Dose rate (kg/ha) | Effect (%) | Glyphosate/ adjuvant ratio |
|---|---|---|---|
| Cocoamide of N,N-bishydroxy-ethyl-1,3-propylenediamine | 0.08 | 40 | 2:1 |
| Cocoamide of N,N-bishydroxy-ethyl-1,3-propylenediamine | 0.15 | 58 | 2:1 |
| Cocoamide of N,N-bishydroxy-ethyl-1,3-propylenediamine | 0.25 | 93 | 2:1 |
| Monoester between polyethyleneglycol (4.5 EO) monococo ether monocarboxymethyl ether and N-methyldiethanolamine | 0.08 | 50 | 2:1 |
| Monoester between polyethyleneglycol (4.5 EO) monococo ether monocarboxymethyl ether and N-methyldiethanolamine | 0.15 | 77 | 2:1 |
| Monoester between polyethyleneglycol (4.5 EO) monococo ether monocarboxymethyl ether and N-methyldiethanolamine | 0.25 | 95 | 2:1 |
| Monoester between polyethyleneglycol (4.5 EO) monococo ether monocarboxymethyl ether and triethanolamine | 0.08 | 52 | 2:1 |
| Monoester between polyethyleneglycol (4.5 EO) monococo ether monocarboxymethyl ether and triethanolamine | 0.15 | 72 | 2:1 |
| Monoester between polyethyleneglycol (4.5 EO) monococo ether monocarboxymethyl ether and triethanolamine | 0.25 | 96 | 2:1 |
| Monoester between polyethyleneglycol (2.5 EO) monococo ether monocarboxymethyl ether and triethanolamine | 0.08 | 48 | 2:1 |
| Monoester between polyethyleneglycol (2.5 EO) monococo ether monocarboxymethyl ether and triethanolamine | 0.15 | 68 | 2:1 |
| Monoester between polyethyleneglycol (2.5 EO) monococo ether monocarboxymethyl ether and triethanolamine | 0.25 | 88 | 2:1 |
| 50% Monoester between polyethyleneglycol (4.5 EO) monococo ether monocarboxymethyl ether and N-methyldiethanolamine + 50% hexyl glucoside | 0.08 | 47 | 2:1 |
| 50% Monoester between polyethyleneglycol (4.5 EO) monococo ether monocarboxymethyl ether and N-methyldiethanolamine + 50% hexyl glucoside | 0.15 | 83 | 2:1 |
| 50% Monoester between polyethyleneglycol (4.5 EO) monococo ether monocarboxymethyl ether and N-methyldiethanolamine + 50% hexyl glucoside | 0.25 | 90 | 2:1 |
| Roundup | 0.08 | 47 | 2:1 |
| Roundup | 0.15 | 60 | 2:1 |
| Roundup | 0.25 | 72 | 2:1 |

EXAMPLE 4

The fungicidal effect of a formulation containing the fungicide Amistar (azoxystrobin) and the cocoamide of N,N-bishydroxyethyl-1,3-propylenediamine was compared to the fungicidal effect of Amistar alone.

A semi-field trial was performed using spring wheat that was artificially inoculated with *Stagonospora nodorum*. The fungicide formulation was applied 4 days after inoculation with a cabin sprayer with flat fan nozzles under a pressure of 4.2 bar, delivering 230 l/ha. Disease assessments were carried out 29 days after inoculation. Attack of *Stagonospora nodorum* was assessed as percent coverage of the second green leaves. Percent control on the fungicide-treated plants was calculated using the formula 100−100× A/B, where A is the attack on treated plants and B is the attack on untreated plants. At a dosage of 0.0625 l/ha of Amistar and 1.5 l/ha of the cocoamide of N,N-bishydroxyethyl-1,3-propylenediamine, there was an improvement in the fungicidal effect as compared to when Amistar was used alone. With Amistar alone 54% control of *Stagonospora nodorum* was obtained whereas for the addition of Amistar and the above-mentioned amidoamine 69.5% control was obtained. No phytotoxicity was seen after adding the adjuvant to Amistar.

What is claimed is:

1. An agrochemical adjuvant of the formula:

$$R1-[O-(EO)_n-CH_2]_x-\underset{\underset{O}{\|}}{C}-Y-(CH_2)_m-N\overset{R2}{\underset{R3}{\diagdown}} \quad (I)$$

where R1 is an aliphatic group containing 7–22 carbon atoms; EO is an ethyleneoxy group; Y is O or NH; R2 and R3 is independently —$CH_2CH_2OH$, —$CH_2CH(CH_3)OH$ or an alkyl group with 1–5 carbon atoms; n is a number between 0–10; x is a number 0–1 provided that when Y is O, then x is 1, and when Y is NH, then x is 0; and m is a number 2–6, provided that when Y is NH, then m is 3–6; or an adduct obtained by reacting one mole of the compound with 1–5 moles of an alkylene oxide having 2–3 carbon atoms.

2. The adjuvant of claim 1 having the formula:

$$R4-O-(EO)_n-CH_2-\underset{\underset{O}{\|}}{C}-O-(CH_2)_m-N\overset{R2}{\underset{R3}{\diagdown}} \quad (II)$$

where R4 is an alkyl group containing 8–22 carbon atoms, n is 2–7, m is a number 2–3 and R2 a R3 is independently —$CH_2CH_2OH$, —$CH_2CH(CH_3)OH$ or an alkyl group with 1–5 carbon atoms.

3. The adjuvant of claim 1 having the formula:

$$R5-\underset{\underset{O}{\|}}{C}-NH-CH_2-CH_2-CH_2-N\overset{CH_2CH_2OH}{\underset{CH_2CH_2OH}{\diagdown}} \quad (III)$$

where R5 is an alkyl group containing 7–21 carbon atoms.

4. An agrochemical composition which comprises at least one agrochemical selected from the group consisting of a pesticide, a fertilizer and mixtures thereof, and which additionally comprises the adjuvant of claim 1.

5. The composition of claim 4 wherein said adjuvant is of the formula where R4 is an alkyl group containing 8–22 carbon atoms, n is 2–7, m is a number 2–3 and R2 and:

$$R4-O-(EO)_n-CH_2-\underset{\underset{O}{\|}}{C}-O-(CH_2)_m-N\overset{R2}{\underset{R3}{\diagdown}} \quad (II)$$

R3 is independently —$CH_2CH_2OH$, —$CH_2CH(CH_3)OH$ or an alkyl group with 1–5 carbon atoms.

6. The composition of claim 4 wherein said adjuvant is of the formula:

$$R5-\underset{\underset{O}{\|}}{C}-NH-CH_2-CH_2-CH_2-N\overset{CH_2CH_2OH}{\underset{CH_2CH_2OH}{\diagdown}} \quad (III)$$

where R5 is an alkyl group containing 7–21 carbon atoms.

7. The composition of claim 4 which additionally comprises an alkyl glycoside $ROG_p$, where R is an alkyl group containing 6–10 carbon atoms, G is a monosaccharide residue and p is a number between 1–5.

8. The composition of claim 4 in solid granular form.

9. The composition of claim 4 in the form of a liquid solution, an emulsion or a suspension.

10. An agrochemical formulation which comprises 0.001–99.9% by weight of an agrochemical, 0–40% by weight of ammonium sulphate and 0.01–70% by weight of an adjuvant, wherein said adjuvant is selected from the group consisting of the adjuvant of claim 1, the adjuvant of formula (II):

$$R4-O-(EO)_n-CH_2-\underset{\underset{O}{\|}}{C}-O-(CH_2)_m-N\overset{R2}{\underset{R3}{\diagdown}} \quad (II)$$

where R4 is an alkyl group containing 8–22 carbon atoms, n is 2–7, m is a number 2–3 and R2 an R3 is independently —$CH_2CH_2OH$, —$CH_2CH(CH_3)OH$ or an alkyl group with 1–5 carbon atoms; the adjuvant of formula (III):

$$R5-\underset{\underset{O}{\|}}{C}-NH-CH_2-CH_2-CH_2-N\overset{CH_2CH_2OH}{\underset{CH_2CH_2OH}{\diagdown}} \quad (III)$$

where R5 is an alkyl group containing 7–21 carbon atoms, and mixtures thereof.

11. The formulation of claim 10 wherein the agrochemical is a pesticide and said pesticide is a strobilurin analogue or a sulphonyl urea.

12. The formulation of claim 10 wherein said agrochemical is a herbicide and said herbicide herbicide is glyphosate (=N-(phosphonomethyl)glycine) or a salt thereof.

13. A fertilizer formulation which comprises 0.0001–99.9% by weight of a fertilizer and 0.0001–70% by weight of an adjuvant, wherein said adjuvant is selected from the group consisting of the adjuvant of claim 1, the adjuvant of formula (II);

$$R4-O-(EO)_n-CH_2-\underset{\underset{O}{\|}}{C}-O-(CH_2)_m-N\overset{R2}{\underset{R3}{\diagdown}} \quad (II)$$

where R4 is an alkyl group containing 8–22 carbon atoms, n is 2–7, m is a number 2–3 and R2 an R3 is independently —$CH_2CH_2OH$, —$CH_2CH(CH_3)OH$ or an alkyl group with 1–5 carbon atoms; the adj uvant of formula (III):

$$R5-\underset{\underset{O}{\|}}{C}-NH-CH_2-CH_2-CH_2-N\overset{CH_2CH_2OH}{\underset{CH_2CH_2OH}{\diagdown}} \quad (III)$$

where R5 is an alkyl group containing 7–21 carbon atoms, and mixtures thereof.

14. The adjuvant of claim 3, where R5 is $CH_3(CH_2)_3CH(CH_2CH_3)$—.

15. The adjuvant of claim 2, where R4 is an alkyl group containing 8–2 carbon atoms, n=2–7, m is 3 and each R2 and R3 independently of each other is an alkyl group with 1–5 carbon atoms.

16. The adjuvant of claim 2, where R4 is an alkyl group containing 8–22 carbon atoms, n=2–7, m is 2, one of the groups R2 and R3 is —$CH_2CH_2OH$ or —$CH_2CH(CH_3)OH$ and the other group is an alkyl group with 1–5 carbon atoms, —$CH_2CH_2OH$ or —$CH_2CH(CH_3)OH$.

* * * * *